United States Patent
Diaz-Astruc et al.

(10) Patent No.: US 8,362,069 B2
(45) Date of Patent: Jan. 29, 2013

(54) COMPOSITIONS COMPRISING AT LEAST ONE AQUEOUS PHASE AND AT LEAST ONE FATTY PHASE WHICH COMPRISES AVERMECTIN COMPOUNDS

(75) Inventors: Fanny Diaz-Astruc, Houston, TX (US); Nathalie Barthez, Nice (FR); Sandrine Segura-Orsoni, Mandelieu (FR)

(73) Assignee: Galderma S.A., Cham (CH)

( * ) Notice: Subject to any disclaimer, the term of this patent is extended or adjusted under 35 U.S.C. 154(b) by 574 days.

(21) Appl. No.: 12/253,509

(22) Filed: Oct. 17, 2008

(65) Prior Publication Data
US 2009/0136574 A1 May 28, 2009

Related U.S. Application Data

(63) Continuation of application No. PCT/FR2007/051128, filed on Apr. 18, 2007.

(30) Foreign Application Priority Data

Apr. 19, 2006 (FR) ..................................... 06 03452

(51) Int. Cl.
*A01N 43/02* (2006.01)
*A01N 45/00* (2006.01)
*A01N 31/08* (2006.01)
(52) U.S. Cl. .......................... 514/450; 514/176; 514/731
(58) Field of Classification Search .................... 424/400
See application file for complete search history.

(56) References Cited

U.S. PATENT DOCUMENTS

2006/0100165 A1* 5/2006 Manetta et al. ................. 514/28

FOREIGN PATENT DOCUMENTS

| EP | 2 374 449 A3 | 2/2012 |
|---|---|---|
| GB | 2310801 A | 9/1997 |
| WO | WO 00/42990 A1 | 7/2000 |
| WO | WO 00/74489 A1 | 12/2000 |
| WO | WO 02/09764 A1 | 2/2002 |
| WO | WO 2004/093886 A1 | 11/2004 |
| WO | WO 2005/089806 A1 | 9/2005 |
| WO | WO 2006/069580 A1 | 7/2006 |
| WO | WO 2007/119028 A3 | 10/2007 |

OTHER PUBLICATIONS

European Search Report with attached European Search Opinion dated Jan. 26, 2012 for EP counterpart of parent application, EP 1113086, 10 pages, in French.

* cited by examiner

*Primary Examiner* — Sreeni Padmanabhan
*Assistant Examiner* — Timothy E Betton
(74) *Attorney, Agent, or Firm* — SNR Denton US LLP

(57) ABSTRACT

Pharmaceutical/dermatological emulsions containing at least one avermectin compound, notably ivermectin, include at least one fatty phase and at least one aqueous phase, the at least one avermectin compound being solubilized in the fatty phase, which emulsions are useful for the treatment of a variety of dermatological conditions/afflictions, in particular rosacea.

22 Claims, No Drawings

COMPOSITIONS COMPRISING AT LEAST ONE AQUEOUS PHASE AND AT LEAST ONE FATTY PHASE WHICH COMPRISES AVERMECTIN COMPOUNDS

CROSS-REFERENCE TO PRIORITY/PCT APPLICATIONS

This application claims priority under 35 U.S.C. §119 of FR 0603452, filed Apr. 19, 2006, and is a continuation of PCT/FR2007/051128, filed Apr. 18, 2007 and designating the United States (published in the French language on Oct. 25, 2007 as WO 2007/119028 A2; the title and abstract were also published in English), each hereby expressly incorporated by reference in its entirety and each assigned to the assignee hereof.

BACKGROUND OF THE INVENTION

1. Technical Field of the Invention

The present invention relates to pharmaceutical compositions based on a compound of the avermectin family comprising at least one fatty phase and at least one aqueous phase, said compound of the avermectin family being solubilized in said fatty phase.

The present invention relates more particularly to ivermectin-based pharmaceutical compositions comprising at least one fatty phase and at least one aqueous phase, the ivermectin being solubilized in said fatty phase.

This invention also relates to the formulation thereof and to the administration of such pharmaceutical compositions for the treatment of dermatological conditions, in particular rosacea.

2. Description of Background and/or Related and/or Prior Art

Ivermectin is a mixture of two compounds belonging to the class of avermectins, 5-O-demethyl-22,23-dihydroavermectin $A_{1a}$ and 5-O-demethyl-22,23-dihydroavermectin $A_{1b}$. They are also known under the trademarks 22,23-dihydroavermectin $B_{1a}$ and 22,23-dihydroavermectin $B_{1b}$. Ivermectin contains at least 80% of 22,23-dihydroavermectin $B_{1a}$ and less than 20% of 22,23-dihydroavermectin $B_{1b}$. This active agent forms part of the class of avermectins, a group of macrocyclic lactones produced by the bacterium *Streptomyces avermitilis* (Reynolds J E F (Ed) (1993) Martindale, The extra pharmacopoeia. 29th Edition. Pharmaceutical Press, London). Avermectins include in particular ivermectin, invermectin, avermectin, abamectin, doramectin, eprinomectin and selamectin.

Ivermectin is more particularly an anthelmintic. It has been administered in humans in the treatment of onchocerciasis caused by onchocerca volvulus, of gastrointestinal strongyloidiasis (anguillulosis) (product Stomectol®) and of human scabies (Meinking T L et al., *N. Engl. J. Med.*, 1995 Jul. 6; 333(1): 26-30 The treatment of scabies with ivermectin) and also in the treatment of microfilaremia diagnosed or suspected in individuals suffering from lymphatic filariosis due to *Wuchereria bancrofti*.

Dermatological conditions are often associated with increased sensitivity of the skin, particularly in the case of rosacea, which is an inflammatory dermatosis that affects mainly the central part of the face and is characterized, inter alia, by reddening of the face, hot flashes and facial erythemia. This type of pathology requires in particular the application of pharmaceutical formulations that are easy to spread and give the user a pleasant feeling of well-being.

Need therefore exists for topical pharmaceutical compositions containing at least one compound of the avermectin family, and more particularly ivermectin, which is completely suited to the pathological condition and specifically to sensitive skin, which is industrially acceptable, i.e., the formulation of which is physically stable (without phase separation) and chemically stable (without modification of the stability of the active agent) and which optimizes the penetration of ivermectin into the skin.

Ivermectin is a compound that is chemically unstable on contact with water. In order to stabilize it, various solutions have been provided in the prior art: EP 0,045,655 proposes forming micelles of surfactants which surround the ivermectin in order to protect it against water; other applications, such as WO 01/60380 or WO 97/26895, propose using aqueous solvents for active agents, such as N-methyl-2-pyrrolidone. Finally, WO 2004/093886 and WO 2005/089806 describe emulsions comprising an oily phase and an aqueous phase, said aqueous phase comprising a micellar active phase containing ivermectin. Unfortunately, these concepts do not allow optimum stability of the ivermectin.

SUMMARY OF THE INVENTION

Ivermectin-based compositions have now been developed, in particular in the form of oil-in-water emulsions, which entirely meet these expectations, comprising a fatty phase dispersed in an aqueous phase, the ivermectin being solubilized in said fatty phase.

These formulations are emulsions which preferably comprise a high percentage of water.

In the compositions according to the invention, the ivermectin is entirely solubilized in the internal oily phase of the emulsion, and this solubilization in the oil globules of the emulsion makes it possible to limit the contact of the ivermectin and the aqueous phase, which those skilled in the art will take care to formulate free of ivermectin solvents. Such compositions are, moreover, very well-tolerated. This advantageously makes it possible to maintain a high percentage of water in order to conserve an aqueous product suitable for the pathological conditions/afflictions targeted.

The present invention therefore features pharmaceutical compositions comprising at least one fatty phase, at least one aqueous phase and at least one compound of the avermectin family, said compound of the avermectin family being solubilized in said fatty phase. The fatty phase is therefore the solvent phase for the active agent.

DETAILED DESCRIPTION OF BEST MODE AND SPECIFIC/PREFERRED EMBODIMENTS OF THE INVENTION

The term "pharmaceutical composition" means a composition which comprises compounds compatible with application to the skin, the mucous membranes and/or the appendages.

The compounds of the avermectin family that are useful according to the invention are selected from among ivermectin, invermectin, avermectin, abamectin, doramectin, eprinomectin and selamectin. Preferably, the compound of the avermectin family is ivermectin.

Preferably, the compositions according to the invention comprise a single aqueous phase and a single fatty phase and is in the form of an oil-in-water emulsion, i.e., the fatty phase being dispersed in the aqueous phase. According to the invention, the term "oil-in-water emulsion" means a system being constituted of a liquid (in this case the fatty phase) which is dispersed in the form of fine droplets in another liquid (in this case the aqueous phase), the two liquids being considered to be insoluble or barely soluble in one another. The particle size is in the region of 1,000 nm (1 µm).

The compositions according to the invention are described as stable emulsions in that these show good physical and chemical stability over time, even at a temperature above ambient temperature (for example, 40° C.), as shown in the examples hereinafter.

In the compositions according to the invention, the ivermectin is present in an amount of from 0.001% to 10%, preferably from 0.001% to 5% by weight relative to the total weight of the composition, and preferably from 0.003% to 2%.

In the compositions according to the invention, the aqueous phase is present in an amount of from 30% to 95% by weight relative to the total weight of the composition.

The fatty phase of the compositions according to the invention comprise at least one fatty phase which is a solvent for the active agent, or oily phase which is a solvent for the active agent, or active phase. The active agent is here understood to be the compound of the avermectin family, preferably ivermectin.

The oily phase which is a solvent for the active agent preferably comprises at least one oily solvent for the active agent different from plant and mineral oils. Thus, the oily phase which is a solvent for the active agent preferably comprises at least one oily solvent for the active agent selected from synthetic oils.

This is because, on the one hand, the active ingredient, and particularly ivermectin, is more successfully solubilized in synthetic oils than in mineral or plant oils, and on the other hand, the compositions obtained with this type of solvent have improved stability.

The oily phase which is the solvent for the active agent thus comprises at least one oily solvent for the active agent, selected in particular from the diisopropyl adipate marketed under the trademark Crodamol DA by Croda, the PPG 15 stearyl ether marketed under the trademark Arlamol E by Uniqema, the octyl dodecanol marketed under the trademark Eutanol G by Cognis and the $C_{12}$-$C_{15}$ alkyl benzoate marketed under the trademark Tegosoft TN by Degussa, and mixtures thereof.

Even more preferably, diisopropyl adipate or PPG-15 stearyl ether, or a mixture of these two compounds, will be used.

Preferably, the active phase of the compositions according to the invention does not comprise any solvent distinct from the oily solvents described above, nor any emulsifier. In particular, it does not comprise any solvent of alcohol or glycol type. This is because the oily solvent(s) described above is (are) sufficient by itself (themselves) to solubilize the active ingredient.

Preferably, the active phase according to the invention contains only at least one oily solvent described above and at least one compound of the avermectin family.

Preferably, the fatty phase comprises at least one oily phase which is a solvent for the active agent (or fatty phase which is a solvent for the active agent). It may also comprise at least one fatty phase which is not a solvent for the active agent. Preferably, the fatty phase comprises an oily phase which is a solvent for the active agent and a fatty phase which is not a solvent for the active agent; alternatively, the fatty phase preferably comprises only an oily phase which is a solvent for the active agent.

The expression "fatty phase which is not a solvent for the active agent" means a lipophilic phase which comprises one or more lipophilic compounds which are not solvents for the active agent, i.e., in which the compounds of the avermectin family have a solubility of less than or equal to 1% by weight relative to the total weight of the non-solvent fatty phase.

The fatty phase which is not a solvent for the active agent comprises at least one lipophilic compound which is not a solvent for the active agent, selected in particular from non-solvent oils, fatty substances, thickeners of the oily phase, and mixtures thereof.

Among the non-solvent oils, exemplary are silicone oils, including cyclomethicone, dimethicone with a viscosity from 20 to 350 cst; mineral oils, including Primol 352 and Marcol 152, manufactured by Esso, and mixtures thereof.

Among the thickening fatty substances, exemplary are the stearyl alcohol marketed under the trademark Speziol C18 by Cognis or the cetyl alcohol marketed under the trademark Speziol C16 by Cognis, waxes, butters and mixtures thereof.

The compositions according to the invention also comprise at least one emulsifier, in order to stabilize the emulsion.

These emulsifiers are amphiphilic compounds which have a hydrophobic part that has an affinity for oil and a hydrophilic part that has an affinity for water, thus creating a link from the two phases. Ionic or non-ionic emulsifiers therefore stabilize oil/water emulsions by adsorbing at the interface and forming lamellar layers of liquid crystals. Their emulsifying capacity is closely linked to the polarity of the molecule. This polarity is defined by the HLB (Hydrophilic/Lipophilic Balance).

These emulsions are in particular selected from the macrogol 21 stearyl ether marketed under the trademark Brij 721 by Uniqema, the macrogol 2 stearyl ether marketed under the trademark Brij 72P by Uniqema, the glyceryl/PEG 100 stearate marketed under the trademark Arlacel 165FL by Uniqema, the ceteareth 20 marketed under the trademark Eumulgin B2 by Cognis, the PEG-6 and PEG 32 palmitostearate marketed under the trademark Tefose 1500 by Gattefossé, the PEG 20 methyl glucose sesquistearate marketed under the trademark Glucamate SSE 20 by Amerchol, polyoxyethylenated fatty acid esters such as the nonionic Arlatone 983 by ICI or the methyl glucose sesquistearate marketed under the trademark Glucate SS by Amerchol.

This type of emulsifier is used at a concentration of from 0.1% to 8% by weight, preferably at a concentration of from 1% to 8% by weight, relative to the total weight of the composition.

The emulsions according to the invention may also comprise coemulsifiers. Among these compounds are, in particular, nonionic sorbitan esters, such as the sorbitan oleate marketed under the trademark Arlacel 80 by ICI or marketed under the trademark Crill 4 by Croda, the sorbitan sesquioleate marketed under the trademark Arlacel 83 by ICI or under the trademark Montane 83 by Seppic, or else sorbitan isostearate; nonionic fatty alcohol ethers having a high HLB, i.e., an HLB greater than or equal to 7, such as ceteareth-20 or ceteareth-12, or fatty alcohol ethers having a low HLB, i.e., an HLB of less than 7, such as steareth-2.

The compositions according to the invention may also comprise a gelling agent.

As gelling agents that can be used, exemplary are the carbomers marketed under the trademark Carbopol 980 NF and Carbopol 981 NF by Noveon, the C10-C30 alkyl acrylate crosspolymer marketed under the trademark Pemulen TR1 by Noveon, the acrylamide gel marketed under the trademark Simulgel 600 by Seppic, the modified celluloses marketed under the trademark Natrosol by Hercules-Aqualon or Methocel by Dow Chemical Company, or else the saccharide biopolymers marketed under the trademark Xantural by SPCI.

Preferably, the compositions according to the invention comprise:

0.01% to 25% of fatty phase which is a solvent for the active agent;
0 to 20% of fatty phase which is not a solvent for the active agent;
1% to 8% of emulsifier;
0 to 5% of a gelling agent;
0.001% to 5% of ivermectin; and
50% to 75% of aqueous phase.

Even more preferably, the compositions according to the invention comprise:

5% to 20% of fatty phase which is a solvent for the active agent;
0 to 10% of fatty phase which is not a solvent for the active agent;
2% to 5% of emulsifier;
0 to 3% of a gelling agent;
0.001% to 2% of ivermectin; and
55% to 70% of aqueous phase.

The compositions according to the invention may also contain additives normally employed in the cosmetics or pharmaceutical field, such as:

humectants such as glycerol, sorbitol or propylene glycol;
preservatives such as methyl para-hydroxybenzoate, propyl para-hydroxybenzoate, butyl para-hydroxybenzoate, phenoxyethanol, benzalkonium chloride, benzyl alcohol, phenylethyl alcohol, chlorhexidine digluconate or chlorephenesin;
anti-irritants, such as allantoin, 18β-glycyrrhetinic acid or DL-alpha-tocopheryl acetate;
moisture regulators;
pH regulators, such as citric acid or sodium hydroxide;
osmotic pressure modifiers;
UV-A and UV-B screens; and
antioxidants, such as α-tocopherol, butylhydroxyanisole (BHA) or butylhydroxytoluene (BHT), vitamin E, propyl gallate or citric acid.

Of course, one skilled in this art will take care to adapt the choice of the additives or the optional compounds to be added to these compositions and also the procedure in such a way that the advantageous properties intrinsically associated with the present invention are not or are not substantially impaired by the addition envisaged.

These additives may be present in the composition at from 0.001% to 20% by weight relative to the total weight of the composition.

The present invention also features a method for preparing the subject compositions, which comprises the following steps:

a) mixing ivermectin with at least one oily solvent, until the ivermectin is solubilized, in order to form the fatty phase;
b) mixing the constituents of the aqueous phase, to homogeneity;
c) incorporating the fatty phase into the aqueous phase so as to form an emulsion.

The fatty phase may comprise an oily phase which is the solvent for the active agent and a fatty phase which is not a solvent for the active agent. In this case, the method comprises, from steps a) and b) above, a step of mixing the oily phase obtained in a) with at least one (supplementary) lipophilic compound which is not a solvent for the active agent, said compound being in particular as described above.

This invention also features administration of the subject compositions for treating dermatological conditions.

The term "dermatological conditions" means more particularly rosacea, acne vulgaris, seborrhoeic dermatitis, perioral dermatitis, acneiform eruptions, transient acantholytic dermatitis and acne miliaris necrotica.

The compositions according to the invention are particularly suitable for the treatment of rosacea, whether regime or regimen.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Study of Active Agent Solubility/Stability

Maximum solubility of ivermectin at T1 hour at ambient temperature (AT) in various oily-phase excipients and 1 month stability at AT and T40° C.

|  | % (w/w) | 1-month stability at AT | 1-month stability at 40° C. |
| --- | --- | --- | --- |
| Diisopropyl adipate | 10.4 | Stable | Stable |
| PPG 15 stearyl ether | 3.3 | Stable | Stable |
| Guerbet alcohol | 2.5 | Not tested | Not tested |
| $C_{12}$-$C_{15}$ alkyl benzoate | 1.6 | Not tested | Not tested |

Example 2

Composition 1

| Phases | INCI Name | % of formula |
| --- | --- | --- |
| A | Purified water | qs 100% |
| A | Glycerol | 7.00 |
| A | Methyl para-hydroxybenzoate | 0.20 |
| A | Disodium edetate | 0.10 |
| A | Allantoin | 0.20 |
| A | Carbomer | 0.15 |
| B | Macrogol 21 stearyl ether | 3.00 |
| B | Glyceryl/PEG 100 stearate | 3.00 |
| B | Propyl para-hydroxybenzoate | 0.10 |
| B | Stearyl alcohol | 2.00 |
| B | Butylhydroxytoluene | 0.10 |
| C | Diisopropyl adipate | 15.00 |
| C | Ivermectin | 1.00 |
| D | Cyclopentasiloxane | 6.00 |
| E | Acrylamide/sodium acryloyldimethyl taurate copolymer & isohexadecane & Polysorbate 80 | 1.00 |
| F | Sodium hydroxide (sol at 10%) | qs pH 6.3 |

Procedure of Composition 1.
Production Under Inactinic Light.
Phase Preparation:
Phase A:
The starting materials of phase A are incorporated in a beaker and heated to 75° C.

Phase B:

The starting materials of phase B are incorporated and then heated to 75° C.

Active Phase C:

The active agent is solubilized in the solvent oil and active phase C is added to phase B.

Emulsification and Neutralization:

Emulsification is carried out by introducing phase B into phase A with Rayneri stirring.

Phases D and then E are introduced at 50° C.

At ambient temperature, neutralization is carried out with sodium hydroxide solution in order to obtain a pH of 6.3, followed by homogenization.

Example 3

Composition 2

| Phases | INCI Name | % of formula |
| --- | --- | --- |
| A | Purified water | qs 100% |
| A | Methyl para-hydroxybenzoate | 0.15 |
| A | Glycerol | 7.00 |
| A | Sodium edetate | 0.10 |
| A | Allantoin | 0.20 |
| A | Carbomer | 0.30 |
| B | Macrogol 2 stearyl ether | 2.50 |
| B | Macrogol 21 stearyl ether | 2.50 |
| B | PPG 15 stearyl ether | 4.00 |
| B | Propyl para-hydroxybenzoate | 0.05 |
| B | Butylhydroxyltoluene | 0.10 |
| C | Diisopropyl adipate | 16.00 |
| C | Ivermectin | 1.00 |
| D | Dimethicone | 1.00 |
| E | Sodium hydroxide (sol at 10%) | qs pH 6.3 |

The procedure of composition 2 is identical to that of composition 1 (Example 3).

Example 4

Composition 3

| Phases | INCI Name | % of formula |
| --- | --- | --- |
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| B | Macrogol 2 stearyl ether | 2.50 |
| B | Macrogol 21 stearyl ether | 2.50 |
| B | PPG 15 stearyl ether | 4.00 |
| B | Propyl paraben | 0.10 |
| B | Butylhydroxytoluene | 0.10 |
| C | Diisopropyl adipate | 16.00 |
| C | Ivermectin | 1.00 |
| D | Dimethicone 200 | 1.00 |
| E | Benzalkonium chloride | 0.05 |
| E | Purified water | 5.00 |
| F | Sodium hydroxide (sol at 10%) | qs pH 6.3 |

The procedure of composition 3 is identical to that of composition 2 (Example 3).

Example 5

Composition 4

| Phases | INCI Name | % of formula |
| --- | --- | --- |
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| B | Macrogol 2 stearyl ether | 2.50 |
| B | Ceteareth 20 | 2.50 |
| B | Propyl paraben | 0.10 |
| C | Diisopropyl adipate | 16.00 |
| C | Ivermectin | 1.00 |
| D | Dimethicone 200 | 1.00 |
| E | Benzalkonium chloride | 0.020 |
| F | Sodium hydroxide (sol at 10%) | qs pH 6.3 |

The procedure of composition 4 is identical to that of composition 3 (Example 4).

Example 6

Composition 5

| Phases | INCI Name | % of formula |
| --- | --- | --- |
| A | Purified water | qs 100% |
| A | Glycerol | 7.00 |
| A | Disodium edetate | 0.10 |
| A | Phenoxyethanol | 1.00 |
| A | Natrosol | 0.50 |
| B | Glyceryl/PEG 100 stearate | 5.00 |
| C | octyldodecanol | 20.00 |
| C | $C_{12}$-$C_{15}$ alkyl benzoate | 5.00 |
| C | Ivermectin | 0.50 |
| F | Sodium hydroxide (sol at 10%) | qs pH 6.3 |

The procedure of composition 5 is identical to that of composition 4 (Example 5).

Example 7

Composition 6

| Phases | INCI Name | % of formula |
| --- | --- | --- |
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| A | Phenoxyethanol | 1.00 |
| B | Macrogol 2 stearyl ether | 2.50 |
| B | Macrogol 21 stearyl ether | 2.50 |
| B | Propyl paraben | 0.10 |
| B | Butylhydroxytoluene | 0.10 |
| B | PPG-15 stearyl ether | 4.00 |

-continued

| Phases | INCI Name | % of formula |
| --- | --- | --- |
| C | Diisopropyl adipate | 16.00 |
| C | Ivermectin | 1.00 |
| D | Dimethicone 200 | 1.00 |
| F | Sodium hydroxide (sol at 10%) | qs pH 6.3 |

The procedure of Example 6 is identical to that of composition 5 (Example 6).

Example 8

Physical and Chemical Stabilities

The physical stability of the formulations according to the invention is measured by macroscopic and microscopic observation of the formulation at ambient temperature (AT) (20-30° C.), 40° C. and 4° C. at T1 month, T2 months, T3 months and T6 months.

At AT, the macroscopic observation makes it possible to guarantee the physical integrity of the products.

The characterization of the finished product is completed by a measurement of the flow point.

A Haake VT550 rheometer with an SVDIN measuring sensor is used.

The rheograms are produced at 25° C. and at the shear rate of $4\ s^{-1}$ ($\gamma$), and by measuring the shear stress. The term "flow point" ($\tau 0$ expressed in Pascals) means the force necessary (minimum shear stress) to overcome the Van der Waals-type cohesion forces and bring about flow. The flow point is comparable to the value found at the shear rate of $4\ s^{-1}$.

These measurements are carried out at T24 h, and at T1 month, T2 months, T3 months and T6 months.

The chemical stability of the compositions is also measured by assaying the ivermectin active agent by HPLC at AT and 40° C. at T0, T1 month, T2 months, T3 months and T6 months. It is compared to that obtained with the cream formulations derived from WO 2004/093886 and the cream-gel formulation derived from WO 2005/089806, below:

Result obtained: R as %.

Composition 1:

| | | Analytical T0: assay 101.7% | Macroscopic appearance pH 24 h: 6.3 Viscosity: $\tau_{(4\ s}{}^{-1}{}_)$ in Pa·$s^{-1}$ | Milk 28 |
| --- | --- | --- | --- | --- |

| | | | T1 month | T2 months | T3 months | T6 months |
| --- | --- | --- | --- | --- | --- | --- |
| AT | | Viscosity: $\tau_{(4\ s}{}^{-1}{}_)$ in Pa·$s^{-1}$ | 35 | 39 | 42 | 51 |
| | | Macroscopic appearance | Compliance | Compliance | Compliance | Compliance |
| | | pH | 6.1 | 6.1 | 6.1 | 6.0 |
| | | Microscopic appearance | Compliance | Compliance | Compliance | Compliance |
| | | Analytical assay | 99.8% | 100.1% | 100.8% | 102.3% |
| 4° C. | | Macroscopic appearance | Compliance | Compliance | Compliance | Compliance |
| | | Microscopic appearance | Compliance | Compliance | Compliance | Compliance |
| 40° C. | | Macroscopic appearance | Compliance | Compliance | Compliance | Compliance |
| | | Microscopic appearance | Compliance | Compliance | Compliance | Compliance |
| | | Analytical assay | 101% | 99.7% | 100.8% | 104.7% |

Composition 2:

| | | Analytical T0: assay 93.6% | Macroscopic appearance pH 24 h: 6.1 Viscosity: $\tau_{(4\ s}{}^{-1}{}_)$ in Pa·$s^{-1}$ | Soft cream 56 |
| --- | --- | --- | --- | --- |

| | | | T1 month | T2 months | T3 months | T6 months |
| --- | --- | --- | --- | --- | --- | --- |
| AT | | Viscosity: $\tau_{(4\ s}{}^{-1}{}_)$ in Pa·$s^{-1}$ | 65 | 70 | 64 | 63 |
| | | Macroscopic appearance | Compliance | Compliance | Compliance | Compliance |
| | | pH | 6.1 | 6.1 | 6.1 | 6.0 |
| | | Microscopic appearance | Compliance | Compliance | Compliance | Compliance |
| | | Analytical assay | 93.6% | 93.9% | 93.9% | 94.4% |
| 4° C. | | Macroscopic appearance | Compliance | Compliance | Compliance | Compliance |
| | | Microscopic appearance | Compliance | Compliance | Compliance | Compliance |
| 40° C. | | Macroscopic appearance | Compliance | Compliance | Compliance | Compliance |
| | | Microscopic appearance | Compliance | Compliance | Compliance | Compliance |
| | | Analytical assay | 92.7% | 94.8% | 91.9% | 94.5% |

Composition 3:

|   |   | T1 month | T2 months | T3 months | T6 months |
|---|---|---|---|---|---|
|   | Analytical T0: assay 99.8% | Macroscopic appearance pH 24 h: 6.2 Viscosity: $\tau_{(4\ s^{-1})}$ in Pa·s$^{-1}$ | | Thick milk 66 | |
| AT | Viscosity: $\tau_{(4\ s^{-1})}$ in Pa·s$^{-1}$ | 58 | 69 | 72 | 61 |
|   | Macroscopic appearance | Compliance | Compliance | Compliance | Compliance |
|   | pH | 6.1 | 6.0 | 6.0 | 6.0 |
|   | Microscopic appearance | Compliance | Compliance | Compliance | Compliance |
|   | Analytical assay | 102.0% | 102.4% | 102.8% | 102.7% |
| 4° C. | Macroscopic appearance | Compliance | Compliance | Compliance | Compliance |
|   | Microscopic appearance | Compliance | Compliance | Compliance | Compliance |
| 40° C. | Macroscopic appearance | Compliance | Compliance | Compliance | Compliance |
|   | Microscopic appearance | Compliance | Compliance | Compliance | Compliance |
|   | Analytical assay | 102.4% | 101.7% | 104.2% | 100.5% |

Composition 4:

|   |   | T1 month | T2 months | T3 months | T6 months |
|---|---|---|---|---|---|
|   | Analytical T0: assay 95.2% | Macroscopic appearance pH 24 h: 6.0 Viscosity: $\tau_{(4\ s^{-1})}$ in Pa·s$^{-1}$ | | Glossy White milk 38 | |
| AT | Viscosity: $\tau_{(4\ s^{-1})}$ in Pa·s$^{-1}$ | 35 | 34 | 41 | 34 |
|   | Macroscopic appearance pH | 6.0 | 6.0 | 6.0 | 5.9 |
|   | Microscopic appearance | Compliance | Compliance | Compliance | 94.4% |
|   | Analytical assay | 95.2% | NR | 100.4% | 94.4% |
| 4° C. | Macroscopic appearance | Compliance | Compliance | Compliance | Compliance |
|   | Microscopic appearance | Compliance | Compliance | Compliance | Compliance |
| 40° C. | Macroscopic appearance | Compliance | Compliance | Compliance | Compliance |
|   | Microscopic appearance | Compliance | Compliance | Compliance | Compliance |
|   | Analytical assay | 104.2% | NR | 101.0% | 98.3% |

Composition 7 (Composition 1 with Active Agent at 0.03%):

|   |   | T1 month | T2 months | T3 months | T6 months |
|---|---|---|---|---|---|
|   | Analytical T0: assay 93.5% | Macroscopic appearance pH 24 h: 6.7 Viscosity: $\tau_{(4\ s^{-1})}$ in Pa·s$^{-1}$ | | Milk 26 | |
| AT | Viscosity: $\tau_{(4\ s^{-1})}$ in Pa·s$^{-1}$ | 27 | 31 | 20 | NR |
|   | Macroscopic appearance | Compliance | Compliance | Compliance | Compliance |
|   | pH | 6.5 | 6.5 | 6.5 | 6.4 |
|   | Microscopic appearance | Compliance | Compliance | Compliance | Compliance |
|   | Analytical assay | 98.4% | 98.3% | 97.4% | 100.6% |
| 4° C. | Macroscopic appearance | Compliance | Compliance | Compliance | Compliance |
|   | Microscopic appearance | Compliance | Compliance | Compliance | Compliance |
| 40° C. | Macroscopic appearance | Compliance | Compliance | Compliance | Compliance |
|   | Microscopic appearance | Compliance | Compliance | Compliance | Compliance |
|   | Analytical assay | 98.6% | 99.5% | 101.0% | 97.8% |

Composition 8 (Composition 2 with Active Agent at 0.03%):

| | Analytical T0: assay 97.6% | Macroscopic appearance pH 24 h: 6.2 Viscosity: $\tau_{(4\,s^{-1})}$ in Pa·s$^{-1}$ | Soft cream 54 | |
|---|---|---|---|---|
| | | T1 month | T2 months | T3 months | T6 months |

| | | T1 month | T2 months | T3 months | T6 months |
|---|---|---|---|---|---|
| AT | Viscosity: $\tau_{(4\,s^{-1})}$ in Pa·s$^{-1}$ | NA | 77 | 80 | 83 |
| | Macroscopic appearance | Compliance | Compliance | Compliance | Compliance |
| | pH | NA | 6.3 | 6.3 | 6.2 |
| | Microscopic appearance | Compliance | Compliance | Compliance | Compliance |
| | Analytical assay | 95.9% | 96.0% | 95.5% | 97.3% |
| 4° C. | Macroscopic appearance | Compliance | Compliance | Compliance | Compliance |
| | Microscopic appearance | Compliance | Compliance | Compliance | Compliance |
| 40° C. | Macroscopic appearance | Compliance | Compliance | Compliance | Compliance |
| | Microscopic appearance | Compliance | Compliance | Compliance | Compliance |
| | Analytical assay | 95.9% | 106.0% (Container not leaktight) | 95.7% | 96.3% |

Example 9

Composition

| Phases | INCI Name | % of formula |
|---|---|---|
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| B | Macrogol 2 stearyl ether | 2.50 |
| B | Macrogol 21 stearyl ether | 2.50 |
| B | Propyl paraben | 0.10 |
| B | Butylhydroxytoluene | 0.10 |
| C | Diisopropyl adipate | 16.00 |
| C | Ivermectin | 1.00 |
| D | Dimethicone 200 | 1.00 |
| E | Benzalkonium chloride | 0.02 |
| E | Purified water | 5.00 |
| F | Sodium hydroxide (sol at 10%) | qs pH 6.3 |

Physical and Chemical Stabilities:

| | Analytical T0: assay 96.8% | Macroscopic appearance pH 24 h: 6.2 Viscosity: $\tau_{(4\,s^{-1})}$ in Pa·s$^{-1}$ | Thick milk 66 |
|---|---|---|---|

| | | T1 month | T3 months | T6 months |
|---|---|---|---|---|
| AT | Viscosity: $\tau_{(4\,s^{-1})}$ in Pa·s$^{-1}$ | 84 | 79 | NA |
| | Macroscopic appearance | Compliance | Compliance | Compliance |
| | pH | 6.2 | 6.1 | 6.1 |
| | Microscopic appearance | Compliance | Compliance | Compliance |
| | Analytical assay | 99.2% | 99.1% | 100% T7 months |
| 4° C. | Macroscopic appearance | Compliance | Compliance | Compliance |
| | Microscopic appearance | Compliance | Compliance | Compliance |
| 40° C. | Macroscopic appearance | Compliance | Compliance | Compliance |
| | Microscopic appearance | Compliance | Compliance | Compliance |
| | Analytical assay | 99.1% | 98.9% | 98.9% T7 months |

Example 10

Composition

| Phases | INCI Name | % of formula |
|---|---|---|
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| B | Macrogol 2 stearyl ether | 2.50 |
| B | Macrogol 21 stearyl ether | 2.50 |
| B | PPG 15 stearyl ether | 4.00 |
| B | Propyl paraben | 0.10 |
| B | Butylhydroxytoluene | 0.10 |
| C | Diisopropyl adipate | 16.00 |
| C | Ivermectin | 1.00 |
| D | Dimethicone 200 | 1.00 |
| E | Benzalkonium chloride | 0.02 |
| E | Purified water | 5.00 |
| F | Sodium hydroxide (sol at 10%) | Qs pH 6.3 |

Physical and Chemical Stabilities:

| | Analytical T0: assay 98.9% | Macroscopic appearance pH 24 h: 6.1 Viscosity: $\tau_{(4\,s^{-1})}$ in Pa·s$^{-1}$ | Thick milk 74 |
|---|---|---|---|

| | | T1 month | T3 months | T6 months |
|---|---|---|---|---|
| AT | Viscosity: $\tau_{(4\,s^{-1})}$ in Pa·s$^{-1}$ | 90 | 80 | NA |

-continued

|  |  |  |  |  |
|---|---|---|---|---|
|  | Macroscopic appearance | Compliance | Compliance | Compliance |
|  | pH | 6.1 | 6.1 | 6.1 |
|  | Microscopic appearance | Compliance | Compliance | Compliance |
|  | Analytical assay | 100.6% | 102.5% | 103.6% T7 months |
| 4° C. | Macroscopic appearance | Compliance | Compliance | Compliance |
|  | Microscopic appearance | Compliance | Compliance | Compliance |
| 40° C. | Macroscopic appearance | Compliance | Compliance | Compliance |
|  | Microscopic appearance | Compliance | Compliance | Compliance |
|  | Analytical assay | 100.7% | 99.5% | 102.3% T7 months |

Example 11

Composition

| Phases | INCI Name | % of formula |
|---|---|---|
| A | Purified water | qs 100% |
| A | Methyl paraben | 0.20 |
| A | Glycerol | 7.00 |
| A | Disodium edetate | 0.10 |
| A | Allantoin | 0.20 |
| A | Carbomer | 0.30 |
| B | Macrogol 2 stearyl ether | 2.50 |
| B | Stearth 20 | 2.50 |
| B | Propyl paraben | 0.10 |
| B | Butylhydroxytoluene | 0.10 |
| C | Diisopropyl adipate | 16.00 |
| C | Ivermectin | 1.00 |
| D | Dimethicone 200 | 1.00 |
| E | Benzalkonium chloride | 0.02 |
| E | Purified water | 5.00 |
| F | Sodium hydroxide (sol at 10%) | Qs pH 6.3 |

Physical and Chemical Stabilities:

| Analytical T0: assay 100.1% | Macroscopic appearance pH 24 h: 6.0 Viscosity: $\tau_{(4\,s^{-1})}$ in Pa·s$^{-1}$ | Thick milk 56 |
|---|---|---|

|  |  | T1 month | T3 months | T6 months |
|---|---|---|---|---|
| AT | Viscosity: $\tau_{(4\,s^{-1})}$ in Pa·s$^{-1}$ | 50 | 48 | NA |
|  | Macroscopic appearance | Compliance | Compliance | Compliance |
|  | pH | 6.0 | 6.0 | 6.0 |
|  | Microscopic appearance | Compliance | Compliance | Compliance |
|  | Analytical assay | 100.1% | 99.9% | 99.6% |
| 4° C. | Macroscopic appearance | Compliance | Compliance | Compliance |
|  | Microscopic appearance | Compliance | Compliance | Compliance |
| 40° C. | Macroscopic appearance | Compliance | Compliance | Compliance |
|  | Microscopic appearance | Compliance | Compliance | Compliance |
|  | Analytical assay | 99.6% | 99.9% | 101.8% |

Example 12

Comparison of the Chemical Stabilities of the Emulsions According to the Invention Versus the Chemical Stabilities of the Creams Described in Patent Application WO 2004/093886

Compositions A and B are compositions as described in Patent Application WO 2004/093886.

Composition A:

| Phases | Function | % in formula |
|---|---|---|
| Fatty phase | Emollient oil | 4.00 |
|  | Emulsifiers | 5.00 |
|  | Fatty alcohol | 6.00 |
|  | Silicone | 0.50 |
|  | Preservative | 0.10 |
| Aqueous phase | Purified water | qs 100% |
|  | Gelling agent | 0.20 |
|  | Humectant | 4.00 |
|  | Antioxidant | 0.05 |
|  | Chelating agent | 0.05 |
|  | Preservative | 0.20 |
| Neutralizing | Base | qs pH 6.30 |
| Active phase | Oleyl alcohol | 2.00 |
|  | Propylene glycol | 2.00 |
|  | Phenoxyethanol | 1.00 |
|  | Ivermectin | 1.00 |

Composition B:

| Phases | Function | % in formula |
|---|---|---|
| Fatty phase | Emollient oil | 4.00 |
|  | Emulsifiers | 5.00 |
|  | Fatty acid | 2.00 |
|  | Self-emulsifiable wax | 1.00 |
|  | Silicone | 0.50 |
|  | Preservative | 0.10 |
| Aqueous phase | Purified water | qs 100% |
|  | Gelling agent | 1.00 |
|  | Humectant | 4.00 |
|  | Antioxidant | 0.05 |
|  | Chelating agent | 0.05 |
|  | Preservative | 0.70 |

| | | | T1 | T2 | T3 | T6 | T9 | |
|---|---|---|---|---|---|---|---|---|
| | | | Base | | | qs pH 6.30 | | |
| Neutralizing | | | | | | | | |
| Active phase | | | Glyceryl triacetate | | | 1.00 | | |
| | | | Propylene glycol | | | 4.00 | | |
| | | | Phenoxyethanol | | | 0.50 | | |
| | | | Ivermectin | | | 1.00 | | |

| Analytical assay | | T0 | T1 month | T2 months | T3 months | T6 months | T9 months | % loss |
|---|---|---|---|---|---|---|---|---|
| Composition A | AT | 101.0% | 100.1% | 99.3% | 98.6% | 95.5% | 91.3% | ±10% |
| Composition B | AT | 99.8% | 88.60% | 83.5% | 77.0% | 79.9% | 69.9% | ±30% |
| Composition 3 according to the invention | AT | 99.8% | 102.0% | 102.4% | 102.8% | 102.7% | Not determined | 0% |
| Composition 5 according to the invention | | 93.5% | 98.4% | 98.3% | 97.4% | 100.6% | 100.9% | 0% |

The results obtained with the formulations according to the invention clearly show that ivermectin solubilized in an oil that is a solvent for the fatty phase is much more stable at ambient temperature (AT) (25° C.) than in the cream formulations, where the ivermectin is solubilized in a micellar phase.

Example 13

Comparison of the Chemical Stabilities of the Emulsions According to the Invention Versus the Chemical Stabilities of the Cream-Gels Described in Patent Application WO 2005/089806

Compositions C and D are cream-gels as described in Patent Application WO 2005/089806.

Composition C:

| Phases | Function | % in formula |
|---|---|---|
| Fatty phase | Emollient oil | 10.00 |
| | Coemulsifiers | 1.00 |
| | Antioxidant | 0.20 |
| | Preservative | 0.10 |
| Aqueous phase | Purified water | qs 100% |
| | Gelling agent | 0.45 |
| | Humectant | 7.00 |
| | Chelating agent | 0.10 |
| | Moisturizer | 0.20 |
| Neutralizing | Base | qs pH 6.30 |
| Active phase | Polysorbate 80 | 4.00 |
| | Propylene glycol | 4.00 |
| | Benzyl alcohol | 1.00 |
| | Ivermectin | 0.10 |

Composition D:

| Phases | Function | % in formula |
|---|---|---|
| Fatty phase | Emollient oil | 10.00 |
| | Coemulsifiers | 1.00 |
| | Antioxidant | 0.20 |
| | Preservative | 0.10 |
| Aqueous phase | Purified water | qs 100% |
| | Gelling agent | 0.45 |
| | Humectant | 5.00 |
| | Chelating agent | 0.10 |
| | Moisturizer | 0.20 |
| Neutralizing | Base | qs pH 6.30 |
| Active phase | Polysorbate 80 | 4.00 |
| | Propylene glycol | 4.00 |
| | Benzyl alcohol | 3.00 |
| | Ivermectin | 0.03 |

| Analytical assay | | T0 | T1 month | T2 months | T3 months | T6 months | % loss |
|---|---|---|---|---|---|---|---|
| Composition C | 40° C. | 99.1% | 97.2% | 98.0% | 94.5% | 95.8% | ±3% |
| Composition D | | 98.0% | 93.1% | 90.6% | 106.9*% | 91.1% | ±7% |
| Composition 3 according to the invention | 40° C. | 99.8% | 102.4% | 101.7% | 104.2*% | 100.5% | 0% |
| Composition 5 according to the invention | | 93.5% | 98.6% | 99.5% | 101.0% | 97.8% | 0% |

*Problem of leaktightness of the container

The results obtained with the formulations according to the invention clearly show that ivermectin solubilized in an oil that is a solvent for the fatty phase is much more stable at 40° C. than in the cream-gels where the ivermectin is solubilized in a micellar phase. However, the ivermectin remains stable in both types of formulation at other temperatures (4° C. and ambient T).

Example 14

Release-Penetration Study

The release-penetration study is carried out with the following 3 formulae:
reference cream: composition A of Example 9,
cream-gel: composition C of Example 10 containing 1% of ivermectin,
emulsion according to the invention: composition 4 according to the invention.

The objective is to compare the in vitro percutaneous absorption of radio-labeled ivermectin through human skin at 0.1% (w/w) in the 3 formulations.

The amount of ivermectin in the epidermis and the stratum corneum is respectively 0.56% for the reference cream formula (composition A), 0.65% for the cream-gel formula (composition C containing 1% of ivermectin) and 0.97% for the emulsion according to the invention (composition 4).

Based on these results, it can be deduced that a formulation effect exists on the release/penetration of ivermectin, even though the latter has a high molecular weight.

The emulsion according to the invention makes it possible to obtain better release-penetration of the ivermectin active agent than that obtained with the reference cream or the cream-gel.

Example 15

Local Tolerance Study

A tolerance study was carried out on placebos of the reference cream (composition A of Example 9), cream-gel (composition C of Example 11 with 1% of phenoxyethanol in place of the benzyl alcohol) and emulsion according to the invention (composition 6 of Example 7) formulations.

Treatment: daily application from day 1 to day 6 of 20 µl of the formulation to the right ear in Balb/c mice.

Evaluation method: clinical observation and measurement of the thickness of the ear of mice from day 2 to day 12.

Weighing of animals on day 1 and on day 12.

The 3 reference cream, cream-gel and emulsion according to the invention placebos tested slightly increase the thickness of the ear, respectively by 14%, 8% to 9%, from the period of day 2 to day 12. The reference cream, cream-gel and emulsion according to the invention formulations are relatively non-irritant in mice and should not be irritant in humans.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A pharmaceutical/dematological emulsion which comprises at least one fatty phase, at least one aqueous phase and at least one avermectin compound, said at least one fatty phase comprising at least one oily solvent other than a mineral or plant oil, said avermectin compound being solubilized in said at least one oily solvent to form an active phase, said active phase being devoid of any solvent for said avermectin compound distinct from said at least one oily solvent; said emulsion consisting essentially of:
a first fatty phase which is a solvent for the at least one avermectin compound, in an amount of from 0.01% to 25% by weight, said first fatty phase consisting essentially of at least one oily solvent selected from the group consisting of diisopropyl adipate, PPG 15 stearyl ether, octyl dodecanol, $C_{12}$-$C_{15}$ alkyl benzoate and mixtures thereof;
a second fatty phase which is not a solvent for the at least one avermectin compound, in an amount of up to 20% by weight, said second fatty phase consisting essentially of at least one member selected from the group consisting of silicone oils, mineral oils, stearyl alcohol, cetyl alcohol, waxes, butters and mixtures thereof;
at least one avermectin compound;
at least one emulsifier, in an amount of 1% to 8% by weight;
a gelling agent, in an amount of up to 5% by weight;
an aqueous phase, in an amount of from 50% to 75% by weight;
and one or more additives selected from the group consisting of humectants, preservatives, anti-irritants, moisture regulators, pH regulators, osmotic pressure modifiers, UV-A and UV-B screens and antioxidants.

2. A pharmaceutical/dematological emulsion which comprises at least one fatty phase, at least one aqueous phase and at least one avermectin compound, said at least one fatty phase comprising at least one oily solvent other than a mineral or plant oil, said avermectin compound being solubilized in said at least one oily solvent to form an active phase, said active phase being devoid of any solvent for said avermectin compound distinct from said at least one oily solvent, said active phase also being devoid of emulsifier; said emulsion consisting essentially of:
a first fatty phase which is a solvent for the at least one avermectin compound, in an amount of from 0.01% to 25% by weight, said first fatty phase consisting essentially of at least one oily solvent selected from the group consisting of diisopropyl adipate, PPG 15 stearyl ether, octyl dodecanol, $C_{12}$-$C_{15}$ alkyl benzoate and mixtures thereof;
a second fatty phase which is not a solvent for the at least one avermectin compound, in an amount of up to 20% by weight, said second fatty phase consisting essentially of at least one member selected from the group consisting of silicone oils, mineral oils, stearyl alcohol, cetyl alcohol, waxes, butters and mixtures thereof;
at least one avermectin compound;
a gelling agent, in an amount of up to 5% by weight;
an aqueous phase, in an amount of from 50% to 75% by weight;
and one or more additives selected from the group consisting of humectants, preservatives, anti-irritants, moisture regulators, pH regulators, osmotic pressure modifiers, UV-A and UV-B screens and antioxidants.

3. The pharmaceutical/dermatological emulsion as defined by claim 1, said avermectin compound being selected from the group consisting of ivermectin, invermectin, avermectin, abamectin, doramectin, eprinomectin and selamectin.

4. The pharmaceutical/dermatological emulsion as defined by claim 3, said avermectin compound being ivermectin.

5. The pharmaceutical/dermatological emulsion as defined by claim 1, which is an oil-in-water emulsion.

6. The pharmaceutical/dermatological emulsion as defined by claim 3, wherein the amount of ivermectin is from 0.001% to 10% by weight, relative to the total weight thereof.

7. The pharmaceutical/dermatological emulsion as defined by claim 1, wherein said avermectin compound is ivermectin and wherein at least the oily solvent diisopropyl adipate is present in said first fatty phase.

8. The pharmaceutical/dermatological emulsion as defined by claim 1, wherein said avermectin compound is ivermectin and wherein a silicone oil is present in said second fatty phase.

9. The pharmaceutical/dermatological emulsion as defined by claim 8, wherein said silicone oil comprises dimethicone.

10. The pharmaceutical/dermatological emulsion as defined by claim 8, wherein at least the oily solvent diisopropyl adipate is present in said first fatty phase.

11. The pharmaceutical/dermatological emulsion as defined by claim 9, wherein at least the oily solvent diisopropyl adipate is present in said first fatty phase.

12. The pharmaceutical/dermatological emulsion as defined by claim 4, comprising from 0.001% to 5% by weight of ivermectin.

13. The pharmaceutical/dermatological emulsion as defined by claim 4, comprising from 0.003% to 2% by weight of ivermectin.

14. The pharmaceutical/dermatological emulsion as defined by claim 1, wherein said first fatty phase is present in an amount of from 5% to 20% by weight, said second fatty phase is present in an amount of up to 10% by weight, said at least one emulsifier is present in an amount of 2% to 5% by weight, said gelling agent is present in an amount of up to 3% by weight and said aqueous phase is present in an amount of from 55% to 70% by weight.

15. The pharmaceutical/dermatological emulsion as defined by claim 14, comprising from 0.001% to 2% of ivermectin.

16. The pharmaceutical/dermatological emulsion as defined by claim 2, said avermectin compound being selected from the group consisting of ivermectin, invermectin, avermectin, abamectin, doramectin, eprinomectin and selamectin.

17. The pharmaceutical/dermatological emulsion as defined by claim 16, said avermectin compound being ivermectin.

18. The pharmaceutical/dermatological emulsion as defined by claim 17, wherein the amount of ivermectin is from 0.001% to 10% by weight.

19. The pharmaceutical/dermatological emulsion as defined by claim 17, comprising from 0.001% to 5% by weight of ivermectin.

20. The pharmaceutical/dermatological emulsion as defined by claim 17, comprising from 0.003% to 2% by weight of ivermectin.

21. The pharmaceutical/dermatological emulsion as defined by claim 14, wherein said first fatty phase is present in an amount of from 5% to 20% by weight, said second fatty phase is present in an amount of up to 10% by weight, said gelling agent is present in an amount of up to 3% by weight and said aqueous phase is present in an amount of from 55% to 70% by weight.

22. The pharmaceutical/dermatological emulsion as defined by claim 21, comprising from 0.001% to 2% of ivermectin.

* * * * *